(12) United States Patent
Myerson et al.

(10) Patent No.: US 7,807,354 B2
(45) Date of Patent: Oct. 5, 2010

(54) LOW VOLUME HYBRIDIZATION

(75) Inventors: Joel Myerson, Berkeley, CA (US);
Paige Lynette Anderson, Belmont, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 258 days.

(21) Appl. No.: 11/322,157

(22) Filed: Dec. 28, 2005

(65) Prior Publication Data

US 2007/0148657 A1  Jun. 28, 2007

(51) Int. Cl.
*C12Q 1/68* (2006.01)
*C12M 1/36* (2006.01)
*C07H 21/04* (2006.01)

(52) U.S. Cl. ............... 435/6; 435/283.1; 435/287.2; 536/23.1

(58) Field of Classification Search .............. None
See application file for complete search history.

(56) References Cited

U.S. PATENT DOCUMENTS

| | | | | |
|---|---|---|---|---|
| 5,059,294 A * | 10/1991 | Lizardi | ............. | 204/458 |
| 5,549,848 A * | 8/1996 | Zeheb et al. | ............. | 252/408.1 |
| 6,121,055 A * | 9/2000 | Hargreaves | ............. | 436/526 |
| 6,171,797 B1 | 1/2001 | Perbost | | |
| 6,180,351 B1 | 1/2001 | Cattell | | |
| 6,232,072 B1 | 5/2001 | Fisher | | |
| 6,242,266 B1 | 6/2001 | Schleifer et al. | | |
| 6,258,593 B1 * | 7/2001 | Schembri et al. | ......... | 435/287.2 |
| 6,323,043 B1 | 11/2001 | Caren et al. | | |
| 6,949,624 B1 * | 9/2005 | Liu et al. | ............. | 530/358 |
| 7,060,439 B2 * | 6/2006 | Gordon | ............. | 435/6 |
| 2003/0087292 A1 | 5/2003 | Chen et al. | | |
| 2004/0241663 A1 | 12/2004 | Peck et al. | | |
| 2005/0176026 A1 | 8/2005 | Franck et al. | | |
| 2005/0271560 A1 * | 12/2005 | Rodgers et al. | ............. | 422/130 |

OTHER PUBLICATIONS

Dressman et al "Transforming single DNA molecules into fluoescent magnetic particles for detection and enumeration of genetic variations" PNAS, 2003, 100(15): 8817-8822.*
Kohne et al "Room temperature method for increasing the rate of DNA reassociation by many thousandfold: The phenol emulsion reassociation technique" Biochemistry, 1977 16(24): 5329-5341.*
Yeh et al., Improving slide-based assays by stirring: Application of liquid-on-liquid mixing to immunofluorescence staining of polytene chromosomes, J. Biochem. Biophys. Methods, 2005, pp. 59-68, vol. 64.
Guttenberg et al., Planar chip device for PCR and hybridization with surface acoustic wave pump, Lab Chip, 2005, pp. 308-317, vol. 5.
European Patent Office Communication dated Apr. 27, 2007, enclosing the European Search Report and Annex dated Apr. 13, 2007, for EP Application No. 06256552, counterpart of U.S. Appl. No. 11/322,157.

* cited by examiner

*Primary Examiner*—B J Forman

(57) ABSTRACT

The present document relates to a system and method of commingling a low volume of a target solution with an array. For example, a quantity of the target solution and a quantity of an immiscible liquid may be introduced into a cavity having an array on an interior surface. The quantities of target solution and immiscible liquid do not fill the volume. Therefore, a gas is contained within the volume. The cavity is then agitated.

22 Claims, 7 Drawing Sheets

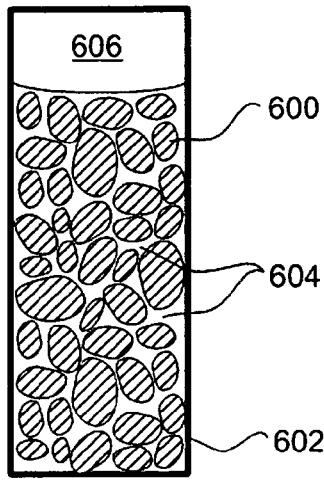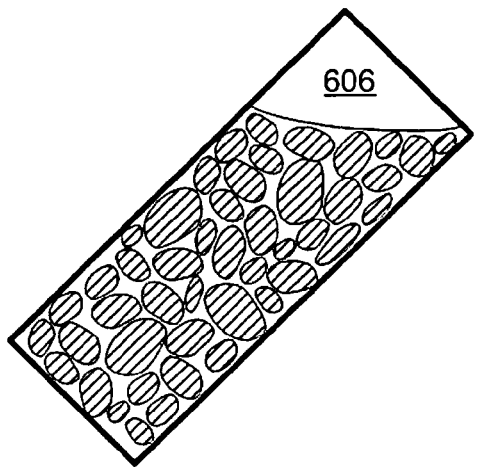
FIG. 6A  FIG. 6B
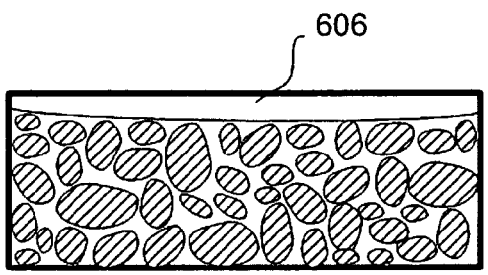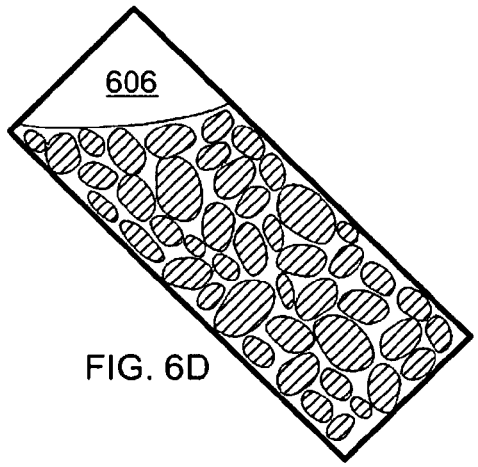
FIG. 6C  FIG. 6D
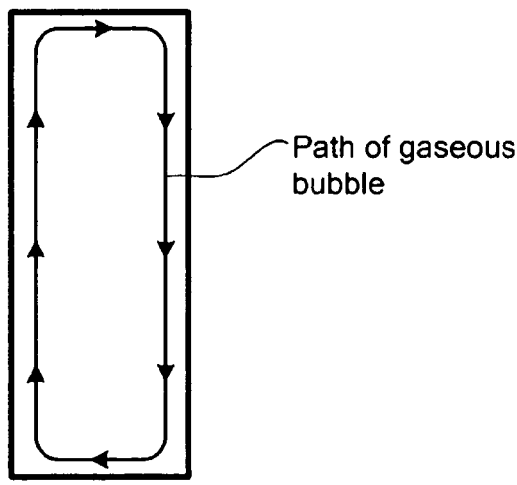
FIG. 6E Compromised Path of gaseous bubble

LOW VOLUME HYBRIDIZATION

BACKGROUND

Arrays are often used, for example, to determine the amount of various analytes contained within a target solution or sample solution. Briefly, an array may be embodied on a substrate that includes a plurality (typically thousands) of regions or features bearing particular chemical moities. Each region bearing a particular chemical moiety may be referred to as a feature, consisting of a quantity of "probes." The chemical composition of each probe is chosen so as to indicate the amount of a given analyte within the target solution. The target solution is permitted to commingle with the array, and thereby to commingle with the various probes thereon. Upon commingling, a probe and its corresponding analyte (if present) bind, and this binding interaction is detected, typically through the use of a label (e.g., a fluorescent label) associated with the analyte molecules. The strength of the signal from a given feature indicates the amount of a corresponding analyte contained within the solution.

The aforementioned scheme is predicated upon the notion that a sufficient amount of the target solution reaches each probe on the array, so that the aforementioned reaction may occur in the time allotted. In some instances, the amount of target material (i.e., the material dissolved to create the solution carrying the various analytes) is limited. For example, in circumstances in which DNA or RNA is used as the target material, its availability is oftentimes limited. Amplification techniques may be used to increase the amount of analyte. However, it may be advantageous to perform the aforementioned hybridization operation without resort to amplification techniques to generate additional target material. It is the general property of array hybridization kinetics that for a given amount of target the hybridization rate will be dependent on target concentration among other things. For example, one may dissolve the relatively small amount of target material in a relatively large volume of solvent, but due to the resulting low concentration of target material, such an approach may lead to a lengthy hybridization time (e.g., 40 hours). On the other hand one may dissolve the relatively small amount of target material in a relatively small volume of solvent resulting in a shorter hybridization time. To ensure that a sufficient amount of the target solution reaches each probe on the array, mixing is often advantageous. It can be difficult to efficiently mix small volumes of target solution on an array surface. Existing mixing techniques, especially for small volumes, require the use of costly specialized equipment. Techniques that do not rely on mixing, such as array hybridization under a statically positioned coverslip, allow for the use of small volumes of solvent, but the beneficial effects of mixing are not present.

As suggested by the foregoing, there exists an opportunity for an improved hybridization technique for use with low volumes of target solution. Such a technique may efficiently hybridize a small quantity of target material held in a small volume of solvent in a relatively short amount of time. Further, such a technique may be carried out using equipment also suitable for larger volume hybridzations.

SUMMARY

In general terms, the present document relates to a method of commingling a low volume of a target solution with an array. According to one embodiment, such a method includes introducing a quantity of the target solution and a quantity of an immiscible liquid into a cavity having an array on an interior surface. The quantities of target solution and immiscible liquid do not fill the volume. Therefore, a gas is contained within the volume. The cavity is then agitated.

According to another embodiment, a hybridization system includes a cavity having an interior surface with an array disposed thereupon. The system also includes an aqueous phase, an immiscible liquid, and a gas contained within the cavity. The cavity contains at least twice as much immiscible liquid as aqueous phase. Also, an agitator is configured to perturb the cavity.

BRIEF DESCRIPTION OF THE DRAWINGS

FIG. 6A depicts an exemplary embodiment of a volume including a desired quantity of liquid bubbles.

FIG. 6B shows the volume of FIG. 6A, after 45° of rotation in the clockwise direction.

FIG. 6C shows the volume of FIG. 6A, after 90° of rotation in the clockwise direction.

FIG. 6D shows the volume of FIG. 6A, after 135° of rotation in the clockwise direction.

FIG. 6E depicts an exemplary path exhibited by a gaseous bubble when the volume is rotated within a particular range of rotational rates.

DETAILED DESCRIPTION

Definitions

Figure 1:
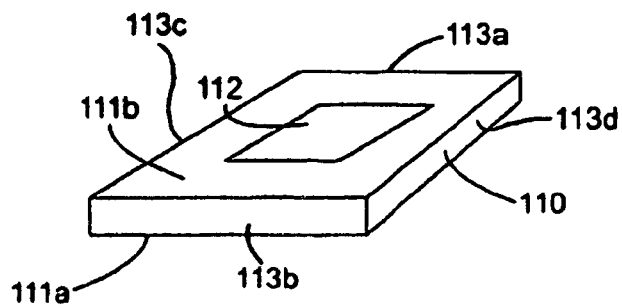
FIG. 1 depicts an exemplary embodiment of a substrate carrying an array.

Unless defined otherwise, all technical and scientific terms used herein have the same meaning as commonly understood by one of ordinary skill in the art to which this invention belongs. Still, certain elements are defined below for the sake of clarity and ease of reference.

The term "biomolecule" means any organic or biochemical molecule, group or species of interest. Exemplary biomolecules include peptides, proteins, amino acids and nucleic acids.

The term "peptide" as used herein refers to any compound produced by amide formation between a carboxyl group of one amino acid and an amino group of another amino acid.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like, or form bicyclic derivatives, as in locked nucleic acids.

The terms "ribonucleic acid" and "RNA" as used herein refer to a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

A "biopolymer" is a polymeric biomolecule of one or more types of repeating units. Biopolymers are typically found in biological systems and particularly include polysaccharides (such as carbohydrates), peptides (which term is used to include oligopeptides, polypeptides and proteins) and nucleic acids (which term is used to include oligonucleotides and polynucleotides) as well as their analogs such as those compounds composed of or containing amino acid analogs or non-amino acid groups, or nucleotide analogs or non-nucleotide groups.

A "biomonomer" references a single unit, which can be linked with the same or other biomonomers to form a biopolymer (e.g., a single amino acid or nucleotide with two linking groups, one or both of which may have removable protecting groups).

An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, DNAs, RNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Each array may cover an area of less than 100 $cm^2$, or even less than 50 $cm^2$, 10 cm or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm, and usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 110 may transmit at least 20%, or 50% (or even at least 70%, 90%, or 95%), of the illuminating light incident on the front as may be measured across the entire integrated spectrum of such illuminating light, or alternatively at 532 nm or 633 nm or other selected wavelengths.

Arrays can be fabricated using drop deposition from pulse-jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein.

The term "sample" as used herein relates to a material or mixture of materials, typically, although not necessarily, in fluid form, containing one or more components of interest.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

Figure 2:
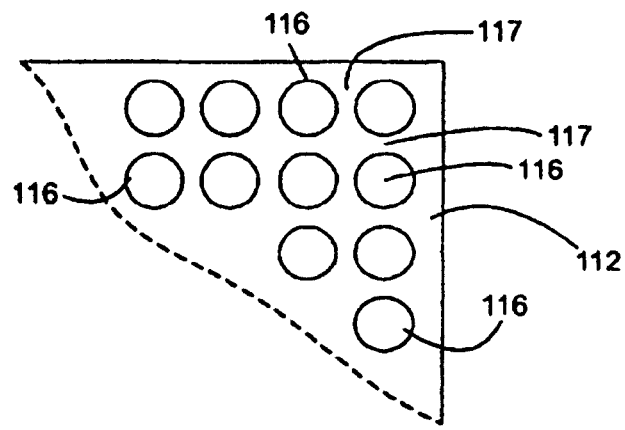
FIG. 2 depicts an enlarged view of a portion of FIG. 1, showing spots or features.
Figure 3:
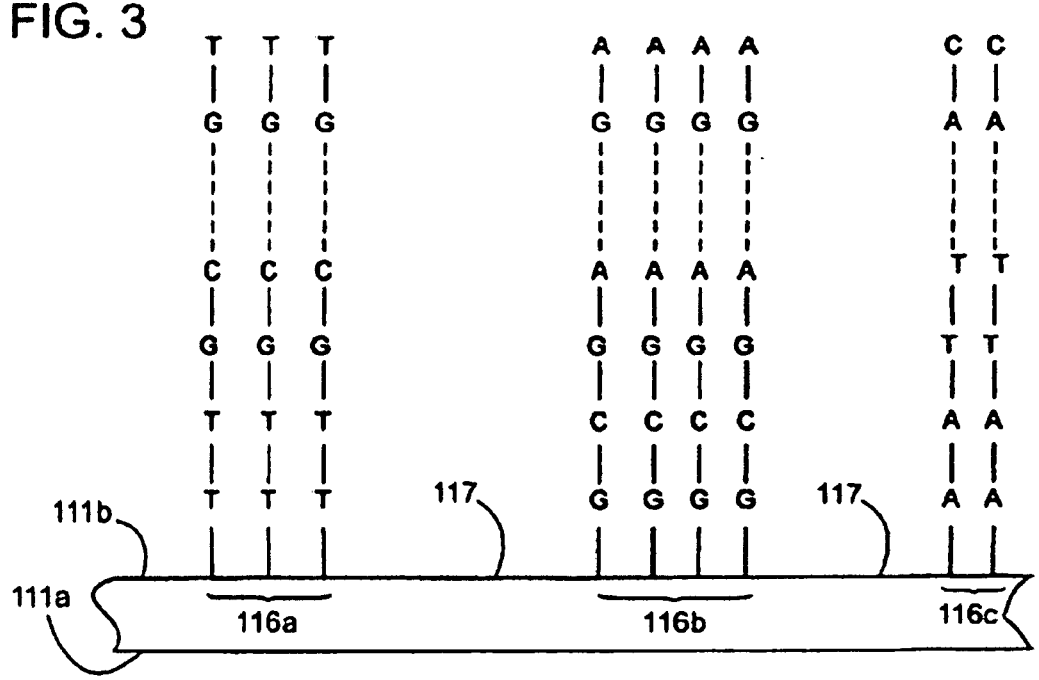
FIG. 3 depicts an enlarged view of a portion of FIG. 1.

An exemplary array is shown in FIGS. 1-3, where the array shown in this representative embodiment includes a contiguous planar substrate 110 carrying an array 112 disposed on front surface 111b of substrate 110. It will be appreciated though, that more than one array (any of which are the same or different) may be present on front surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the front surface 111b, with regions of the front surface 111b adjacent the opposed sides 113c, 113d and leading end 113a and trailing end 113b of slide 110, not being covered by any array 112. A rear surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of biopolymers, e.g., in the form of polynucleotides. As mentioned above, all of the features 116 may be different, or some or all could be the same. The interfeature areas 117 could be of various sizes and configurations, or there may be no interfeature area 117 present, that is features 116 may be directly adjacent to one another. Each feature carries a predetermined biopolymer such as a predetermined oligonucleotide (which includes the possibility of mixtures of oligonucleotides). It will be understood that there may be a linker molecule (not shown) of any known types between the rear surface 111b and the first nucleotide.

Substrate 110 may carry on rear or front surface 111a or 111b, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

The term "substrate" as used herein refers to a surface upon which marker molecules or probes, e.g., an array, may be adhered. Glass slides are the most common substrate for use in connection with the subject matter of the present document, although fused silica, silicon, plastic and other materials are also suitable.

Description of Embodiments

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Figure 4A:
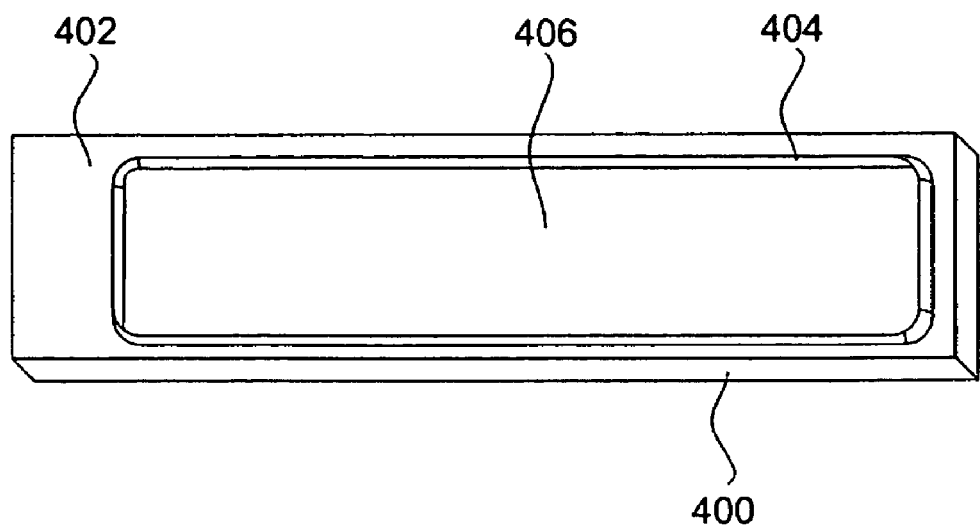
FIG. 4A depicts an exemplary embodiment of a gasket substrate.

As described previously, hybridization occurs by virtue of commingling a target solution with the various probes contained in an array. According to some embodiments, this is accomplished by filling a cavity defined by a gasket slide and an array slide with a target solution. An example of a gasket slide 400 is depicted in FIG. 4A. As can be seen from FIG. 4A, the gasket slide 400 depicted therein is generally rectangular in shape, and possesses an upper surface 402, which is substantially planar. Generally, the gasket slide 400 may be of any shape. According to some embodiments, the gasket slide 400 may be made of glass, although other suitable materials may be used as well, e.g., fused silica, plastic, etc.

A gasket 404 is disposed on the top surface of the gasket slide 400. The gasket 404 may be made of rubber, for example, or of any other suitable material known to be inert. The gasket 404 may extend generally along the periphery of the upper surface 402, or may form a closed shape, extending along only a portion of the upper surface 402, as is the case in the particular embodiment shown in FIG. 4A. The upper surface 402 of the gasket slide 400 and the gasket 404 cooperate to form a region 406 into which a target solution may be introduced. The gasket 404 forms a seal with the upper surface 402 of the gasket slide 400, preventing the target solution from exiting the region 406.

Figure 4B:
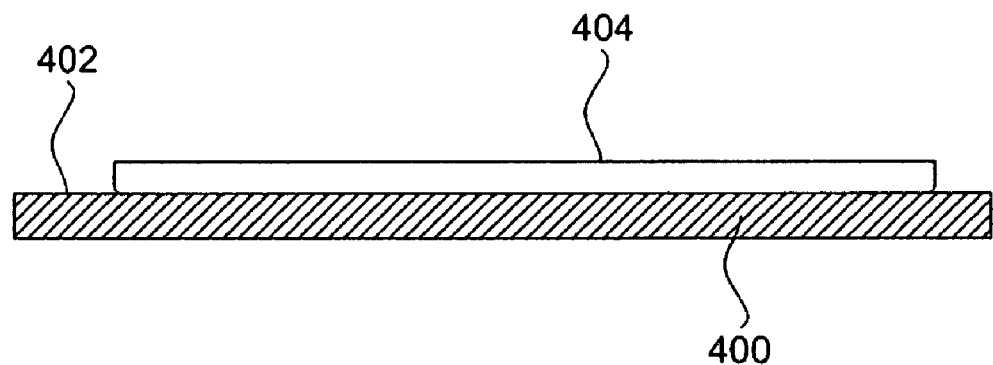
FIG. 4B depicts a side view of an exemplary embodiment of a gasket substrate.
Figure 4C:
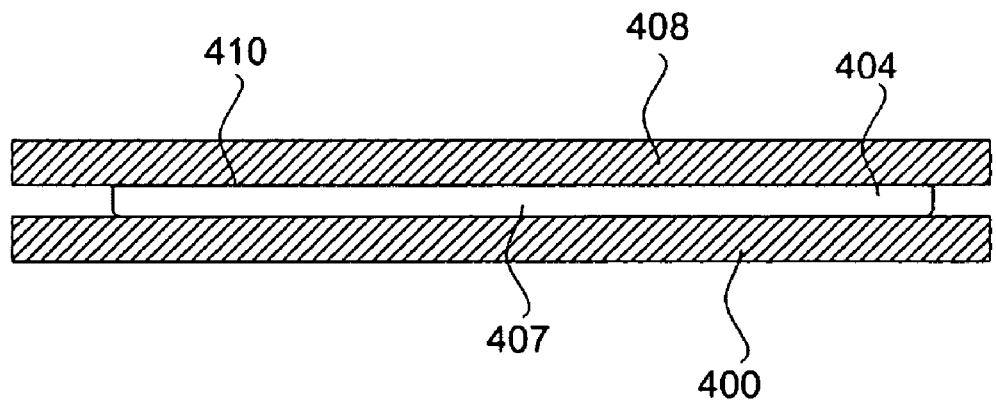
FIG. 4C depicts an exemplary embodiment of a sandwich.

FIG. 4B is a depiction of a side view of the gasket slide 400 shown in FIG. 4A. As can be seen from FIG. 4B, the gasket 404 projects upwardly from the upper surface 402 of the gasket slide 400, thereby defining the aforementioned open volume. It should be noted that the figures presented herein, including FIGS. 4A-4C, are not drawn to scale. Also, certain features have been exaggerated for the sake of illustration. For example, the gasket 404 has been drawn as exaggeratedly large for the sake of illustration.

FIG. 4C depicts a "sandwich" in which hybridization occurs. The sandwich includes the aforementioned gasket slide 400 and an array-containing substrate 408. According to some embodiments, the substrate 408 is also generally rectangular in shape (although this need not be the case), and has a generally planar lower surface 410 containing one or more arrays, as described with reference to FIGS. 1-3. The substrate 408 is placed atop the gasket slide, as shown in FIG. 4C, thereby closing the aforementioned region 406, forming a cavity 407. Since the lower surface 410 of the substrate 408 includes the array, the array is in fluid communication with the target solution contained in the cavity 407, when the substrate is positioned in the "sandwich" configuration shown in FIG. 4C.

The sandwich depicted in FIG. 4C defines a cavity 407 suitable for high volume hybridization. According to one embodiment, the cavity defined by the sandwich is 600 microliters. It is to be understood that this cavity may be greater or lesser than 600 microliters. For example, the cavity could be as small as about 10 microliters and as large as about 2000 microliters. For the sake of illustration, the cavity defined by the sandwich is described herein as being 600 microliters.

It is also to be appreciated that other examples of hybridization cavities exist, other than the particular example depicted in FIGS. 4A-4C. For example, the target solution may be added into a pre-existing cavity, through appropriate openings present in an otherwise closed hybridization cell. Alternatively, the entire array may be completely immersed in the target solution, wherein the hybridization volume surrounds the entire substrate. The low volume hybridization techniques described herein may be used in association with other such hybridization volumes. The particular exemplary hybridization volume discussed herein is referred to for illustrative purposes only.

According to one known high volume hybridization operation, the cavity 407 defined by the sandwich may be filled with 500 microliters of a solution carrying the target material. The aforementioned solution may consist of a target material diluted to 250 microliters (i.e., diluted in a solution of water and appropriate blocking agents) and another 250 microliters of an appropriate hybridization buffer, bringing the total solution volume to about 500 microliters held in a 600 microliter cavity. One example of an appropriate hybridization buffer is Agilent 2X Hyb Buffer, (p/n 5185-5973). Hybridization buffers may include superwetting agents, as described in U.S. patent application Ser. No. 11/082,476, entitled "COMPOSITION AND METHOD FOR ARRAY HYBRIDIZATION," filed on Mar. 16, 2005, which is hereby incorporated by reference for all it teaches. Other hybridization buffers are known and may be used in connection with the schemes taught herein.

In contrast, according to one embodiment of the low volume hybridization scheme described herein, the cavity defined by the sandwich is filled with a 75 microliter aqueous phase and a 425 microliter non-aqueous phase. The aqueous phase includes a target material diluted to 37.5 microliters (again, diluted in a solution of water and appropriate blocking agents) and an additional 37.5 microliters of an appropriate hybridization buffer. Again, one example of an appropriate hybridization buffer is the aforementioned Agilent 2X Hyb Buffer. The aqueous phase may also include a substantial portion of organic component, such as 50% formamide. The non-aqueous phase is made up of approximately 400 microliters of a substantially immiscible liquid. Examples of a suitable immiscible liquid include perfluorocarbon liquids, such as CT-180 (Asahi Glass), HT-180 (Solvey-Solexis), FC-40 and FC-43 (3M) and hydrofluorocarbon fluids, such as ZT-180 (Solvey Solexis) and Novec HFE-7500 (3M). Other suitable immiscible liquids exist, and are generally characterized by exhibiting relatively low surface tension. For example, the surface tension may be less than about 20 dynes/cm. Typically, the kinematic viscosity (25° C.) of a suitable immiscible liquid may be less than 2 centistokes, but substantially higher viscosities may also be used. Boiling points of suitable liquids may vary, but typically will be higher than the temperature at which the hybridization is performed, although liquids with lower boiling points may be used if the system is well sealed. One particularly effective class of immiscible liquids are members of the class of perfluorinated liquids that include Galden®, Fomblin®, Fluorinert® Solvents, perfluorinated hydrocarbons, perfluorinated polyethers, perfluorinated alkylamines, perfluorinated liquids, and perfluoro-compounds based on the polymerization and oxidation of 1,1,2,2,3,3-hexafluoropropene. Another particularly effective class of immiscible liquids are members of the class of partially fluorinated hydrofluorocarbon liquids, which include H-Galden®, Novec® Engineered Fluids, hydrofluoropolyethers, compounds of the general structure $(HCF_2O-CF_2O)_n(CF_2CF_2O)_m-CF_2H$, and compounds of the general hydrofluoroether structure $C_nF_{n+2}-O-C_mH_{m+2}$.

Such liquids are generally non-flammable and exhibit low toxicity. (Hybridization is carried out in a heated oven, and non-flammability is therefore a desirable quality). If flammability is not an issue, other immiscible liquids, such as hydrocarbon liquids, may be suitable. The immiscible liquid and the aqueous phase may exhibit substantially different contact angles or surface tensions. For example, the immiscible liquid may exhibit a surface tension of less than about 20 dynes/cm, while the aqueous phase exhibits a surface tension of greater than about 20 dynes/cm. Stated qualitatively, for the sake of example, the difference between the surface tensions of the immiscible liquid and the aqueous phase may be such that, if the same 10 μl volume of aqueous phase and immiscible liquid are deposited upon a slide, the immiscible liquid may spread out to cover a surface area of greater than about twice the surface area covered by the spread of the aqueous phase. The role of the immiscible liquid is discussed below. It should be noted that per the present low volume hybridization technique, the target material is diluted to a much lesser extent than per the aforementioned exemplary known high volume technique (diluted to only 75 μl, as opposed to 500 μl). Thus, per the low volume hybridization scheme, a given quantity of target material is almost seven times as concentrated in its aqueous phase, than in the solution called out per the high volume hybridization technique.

Upon mixing of the target-containing solution and the immiscible liquid, they form phases—an aqueous phase, which holds the target material in solution, and a non-aqueous phase made up of the immiscible liquid. As discussed below, during hybridization, the sandwich is agitated by an agitator. For example, it may be rotated on a carousel or spun by a rotator. The non-aqueous phase responds to such agitation by fragmenting into a plurality of bubbles (i.e., bubbles made up of the immiscible liquid). These liquid bubbles cooperate with an air bubble to spread the aqueous phase (and therefore the target material held in solution therein) across the lower surface 410 of the substrate 408. Thus, the target material is spread evenly across the entirety of the array (or arrays) disposed upon the lower surface 410 of the substrate 408. (An exemplary process of agitating the sandwich is discussed further, below.)

It is to be noted that more than one mutually immiscible liquids may be used in conjunction with the techniques described herein. For example a fluorocarbon liquid may be used as a first immiscible liquid, and a hydrocarbon liquid may be used as a second immiscible liquid. Per such a scenario, the first and second immiscible liquids are immiscible with respect to one another, and are also immiscible with respect to the aqueous phase. Thus, when agitated, the hybridization cavity exhibits two different types of liquid bubbles— liquid bubbles made up of the first immiscible liquid, and liquid bubbles made up of the second immiscible liquid.

Figure 5A:
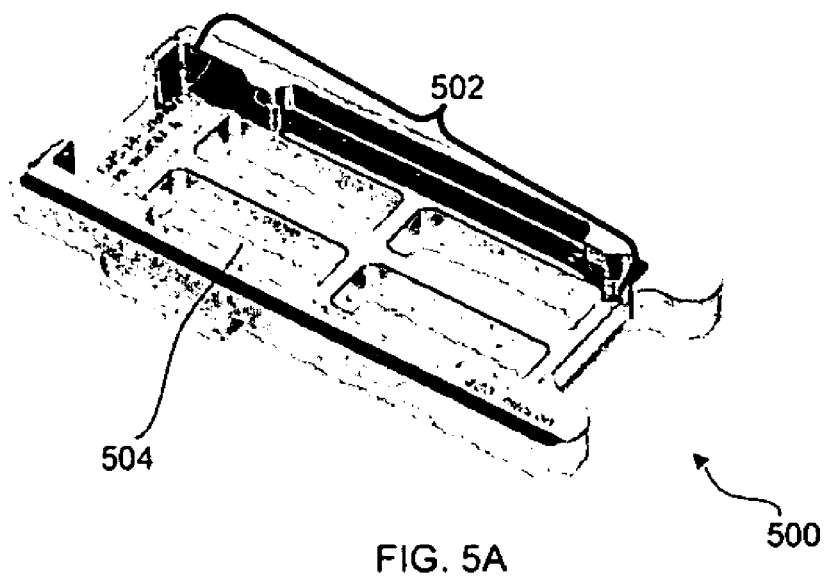
FIG. 5A depicts an exemplary embodiment of a chamber base.
Figure 5B:
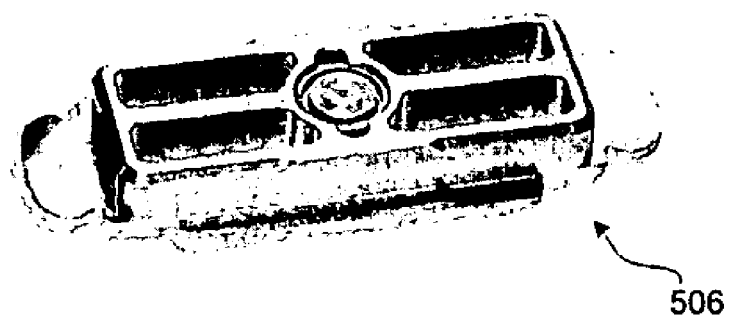
FIG. 5B depicts an exemplary embodiment of a chamber cover.
Figure 5C:
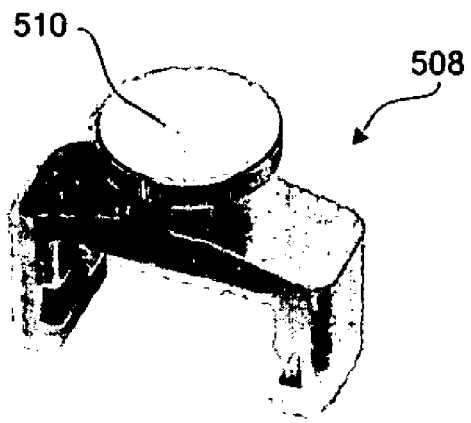
FIG. 5C depicts an exemplary embodiment of a clamp assembly.

Prior to rotation, the sandwich may be placed within a hybridization chamber, or some other system of clamping the sandwich together may be used. FIGS. 5A-5C depict exemplary embodiments of various components of a hybridization chamber designed for high volume hybridization, but which function to permit low volume hybridization, as described herein. A chamber base 500 is depicted in FIG. 5A. The chamber base 500 includes a recessed region 502, which is dimensioned to receive the sandwich, such as the sandwich shown in FIG. 4C.

After the sandwich is placed in the chamber base 500, the chamber cover 506 (FIG. 5B) is placed atop the chamber base 500, thereby securing the sandwich in the recess 502. A clamp assembly 508 is used to secure the chamber base 500 to the chamber cover 506, thereby keeping the sandwich from falling apart. (The clamping action of the assembly 508 is controlled by rotation of a thumbscrew 510 located thereupon.)

As can be seen from FIG. 5A, the recessed region 502 of the chamber base 500 includes four voids (only one of which has been identified with reference numeral 504). The voids 504 serve as windows, which permit viewing of the sandwich when the hybridization chamber is clamped closed.

As mentioned previously, after the sandwich has been placed in the hybridization chamber, and the hybridization chamber is clamped closed, the chamber is seated in an agitator, such as a carousel or rotation device. For the sake of illustration only, the remainder of the specification refers to the agitation process as occurring via rotation of the hybridization chamber by a carousel or rotation device. The rotation device rotates the hybridization chamber at a selectable rotation rate. The rotation device may be located within an oven, so that the temperature of the sandwich may be controlled during the hybridization process (for example, the oven may be set at a temperature of 65° C. during hybridization). The rotation device may be suitable for holding multiple hybridization chambers simultaneously (for example, Agilent rotator rack, p/n #G2530-60029, may be situated within oven, Agilent p/n #G2545A).

The desired rate of rotation of the hybridization chamber is a function of, amongst other variables, the volume and chemical composition of the immiscible liquid, the volume and chemical composition of the target solution, the shape and thickness of the cavity, the volume of the gaseous bubble, and the temperature at which the hybridization is performed. As mentioned previously, upon rotation of a hybridization chamber, the immiscible liquid phase fragments into a plurality of liquid bubbles. Since the liquid bubbles are immiscible in the aqueous phase, the aqueous phase fills the regions not filled by the liquid bubbles (i.e., the aqueous phase occupies the regions in between the bubbles). Thus, the liquid bubbles serve the function of spreading the aqueous phase substantially evenly across the volume in which they are held. For example, FIG. 6A depicts a frontal view of the volume. As can be seen in FIG. 6A, a plurality of liquid bubbles 600 are contained within the gasket 602, which defines four sides of the volume (the surfaces 402 and 410 of the substrates 400 and 408 define the other two surfaces). The aqueous phase 604 fills the regions in between the liquid bubbles. A gaseous bubble 606 floats at the upward region of the volume. The gaseous bubble is referred to as an "air bubble" herein, because air is a suitable gas for the purposes of the present low volume hybridization techniques described herein. It should be understood that gasses in addition to air may be used in conjunction with the low volume hybridization techniques described herein. It should be also noted that underneath the liquid bubbles and the air bubble a film made up of the aqueous phase may extend across the surface of the array-carrying surface, i.e., surface 410 of substrate 408.

When rotated within a particular range of rotational frequencies, the immiscible liquid fragments into a quantity of liquid bubbles that exhibit free motion during rotation of the chamber. Considering a bubble having a periphery at time to, that bubble exhibits "free motion," if, within about ten minutes, it travels to a location such that its periphery falls entirely outside of the aforementioned periphery at time to. For example, FIG. 6B depicts the cavity after about 45° of clockwise rotation. As can be seen, the air bubble 606 has floated to the upward-most region of the volume, and in so doing has displaced the liquid bubbles 600 and the aqueous phase 604. The process of displacing the liquid bubbles 600 serves as a "stirring" action, which moves the aqueous phase about the cavity. FIGS. 6C and 6D depict the cavity after 90° and 135° of clockwise rotation. As can be seen, the air bubble 606 continues to move to the upward-most region of the cavity, thereby efficiently stirring the aqueous phase, and the liquid bubbles 600 continue to be displaced by the air bubble 606. The liquid bubbles 600 exhibit free motion, thereby mixing and distributing the aqueous phase substantially evenly throughout the cavity, and therefore over the array-carrying surface 410 of the substrate 408.

Thus, as shown in FIG. 6E, when rotated within a particular range of rotational frequencies, the air bubble 606 moves substantially along the periphery of the cavity, i.e., substantially follows the gasket 602, and thereby stirs the liquid bubbles and aqueous phase. This state of affairs permits the relatively low volume of aqueous solution (e.g., 75 µl) to be effectively distributed throughout the relatively large volume of the cavity defined by the sandwich (e.g., 600 µl), and therefore allows for effective and efficient low volume hybridization to occur within a hybridization chamber and cavity designed for high volume hybridization. Furthermore, the mixing during the hybridization was achieved using the same equipment suitable for a high volume hybridization.

It should be noted that FIGS. 6A-6D are not drawn to scale, and that certain features therein have been exaggerated for the sake of illustration. For example, the regions between the various liquid bubbles 600 are drawn as exaggeratedly large for the sake of illustration. According to some embodiments, the volume contains a ratio of immiscible liquid to aqueous phase of between about 2:1 to 20:1. Therefore, if depicted to scale, the spaces between the various liquid bubbles 600 may appear much smaller than those shown in FIGS. 6A-6D.

It should also be noted that if the hybridization chamber is rotated at a rotational rate below the particular range the immiscible liquid may fragment into a quantity of bubbles too few to effectively spread the aqueous phase about the cavity. In fact, if rotated sufficiently slowly, the immiscible liquid may fail to form bubbles at all.

Figure 7A:
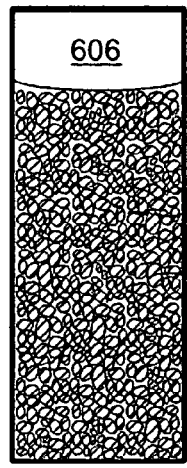
FIG. 7A depicts an exemplary embodiment of a volume including a quantity of liquid bubbles that compromises the motion of a gaseous bubble.
Figure 7B:
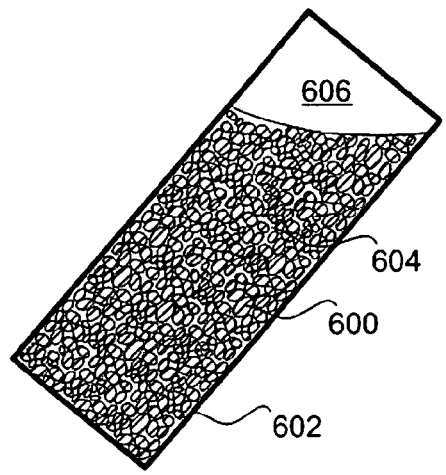
FIG. 7B shows the volume of FIG. 7A, after 45° of rotation in the clockwise direction.
Figure 7C:
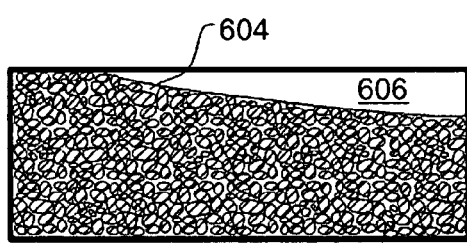
FIG. 7C shows the volume of FIG. 7A, after 90° of rotation in the clockwise direction.
Figure 7D:
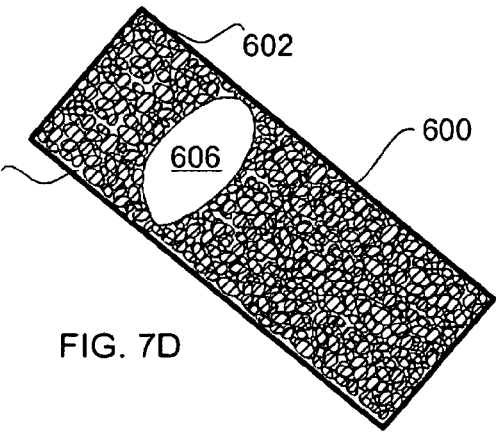
FIG. 7D shows the volume of FIG. 7A, after 135° of rotation in the clockwise direction.
Figure 7E:
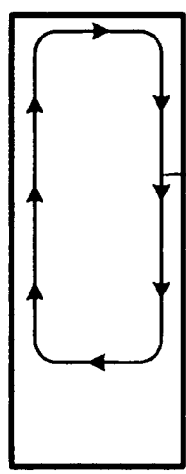
FIG. 7E depicts an exemplary path exhibited by a gaseous bubble when the volume is rotated at a rate greater than a particular range of rotational rates.

On the other hand, if rotated too quickly, the immiscible liquid may fragment into a great plurality of liquid bubbles. Under such circumstances, the motion of the air bubble may be compromised, and a portion of the liquid bubbles end up stuck at one end of the cavity. For example, FIG. 7A depicts a side view of the cavity shown in FIGS. 6A-6C. As can be seen in FIG. 7A, a plurality of liquid bubbles 600 are contained within the gasket 602. As was the case in FIGS. 6A-6D, the aqueous phase 604 fills the regions in between the liquid bubbles, and an air bubble 606 floats at the upward region of the cavity. FIGS. 7B-7D depict the motion of the air bubble 606 as the hybridization chamber is rotated through 45°, 90°, and 135°, respectively. As can be seen from FIG. 7B-7D, as the hybridization chamber rotates, the air bubble 606 is unable to travel a path whereby it consistently reaches the upward-most portion of the cavity. Such a state of affairs is less desirable (but still within the scope of the present low volume hybridization technique), because the stirring action of the bubble does not directly affect the entirety of the cavity, meaning that hybridization may not be as efficient in the unreached regions. (It should again be noted that FIGS. 7A-7D are not drawn to scale, and that certain features therein have been exaggerated for the sake of illustration.) In sum, when rotated too quickly, the air bubble 606 tends to travel a course, whereby it fails to reach one or both ends of the volume, as shown in FIG. 7E.

While not wishing to be bound to any particular theory regarding causation of the effect depicted in FIGS. 7A-7E, it is believed that the compromised motion of the air bubble 606 is influenced by the disparity of surface tensions exhibited by the immiscible liquid 600 and the aqueous phase 604. It is known that as the disparity between surface tensions between two fluids increases, more energy is consumed at the interface between the fluids, as surfaces of the fluids move across one another. Therefore, it is believed that, as the immiscible liquid fragments into a great plurality of bubbles, the number of interfaces between the aqueous phase and immiscible liquid increases, and that the quantity of energy required to move the air bubble therefore increases, making it more difficult for the air bubble to consistently float to the upward-most region of the volume.

As mentioned previously, the desired rate of rotation of the hybridization chamber is a function of, amongst other variables, the size of the air bubble. In general, if the air bubble is made larger, it can be more effective at displacing the liquid bubbles in the cavity. Under these conditions, it is advantageous that the target solution leave a film behind on the array surface, or at least on the array features, underneath the air bubble. It can be advantageous to add various surfactants and/or superwetting agents to the target solution in order to facilitate this. Under some conditions, if the air bubble is substantially larger than 50% of the volume of the cavity, the target solution may not be spread uniformly over the entire surface of the substrate during the rotation of the hybridization chamber. In that case, the air bubble is preferably no larger than approximately 50% of the volume of the cavity.

As mentioned previously, the desired rate of rotation of the hybridization chamber is a function of, amongst other variables, the chemical composition of the immiscible liquid. For example, using the Agilent hybridization chambers (p/n G2534A), gasket slides (p/n G2534-60003) and arrays (p/n G4410B), with a 500 µl total fluid volume (75 µl target solution and 425 µl immiscible liquid), two different immiscible liquids lead to differences in bubble formation as well as differences in efficiency of mixing when different rates of rotation are used. When the immiscible liquid CT-180 is used at a rotation rate of 10 revolutions per minute (RPM), the liquid fractures into on the order of 100 bubbles. However, when rotated at 15 RPM, CT-180 fragments into on the order of 300 bubbles, which compromises the motion of the air bubble, as shown in FIGS. 7A-7D. Thus, if CT-180 is used as the immiscible liquid, it is preferable (but not necessary) to rotate the hybridization chamber at about 10 RPM, but not as fast as 15 RPM. On the other hand, if ZT-180 is used as the immiscible liquid, when rotated at 10 RPM it fails to form any bubbles. In this case, rotation rates greater than 15 RPM are required for bubble formation. Therefore, in contrast to CT-180, it is preferable to rotate ZT-180 at a rotational rate greater than 15 RPM.

The inventors of the present low volume hybridization scheme have found that the preferable rotational rate range may be altered by combining two or more immiscible liquids. For example, by using a 1:1 mixture of CT-180 and ZT-180, the preferable range of rotation rates is 15-18 RPM. In addition, the use of combinations of immiscible liquids may provide additional benefits such as more robust and uniform mixing.

It should also be noted that, according to the volume and chemical composition of the immiscible liquid, the volume and chemical composition of the target solution, the shape and thickness of the cavity, the volume of the air bubble, and the temperature at which the hybridization is performed, the air bubble may fracture into a plurality of smaller air bubbles at certain rates of rotation. According to some embodiments, it may be desired to rotate the hybridization chamber at a rate chosen so that the air bubble does not fracture.

EXAMPLES

The present low volume hybridization technique has been tested experimentally, and has shown favorable results.

Example 1

Sample Preparation

According to one experiment, 0.5 ug Promega Male (p/n G1471) and Female (p/n G1521) gDNA were labeled with Cy5 and Cy3 dUTPs respectively as per the Agilent SOP labeling method as outlined in the 'Oligonucleotide Array-Based CGH for Genomic DNA Analysis' Protocol Version 2.0 (August 2005). In short: The gDNAs were digested with AluI & RsaI restriction enzymes, the restriction fragments were purified using the QIAGEN QIAprep Spin Miniprep kit (p/n 27106), DNA was quantitated using the Nanodrop ND-1000 spectrophotometer, 0.5 ug of the digested fragments were aliquoted for each labeling reaction, fragments were then labeled using the Invitrogen BioPrime Array CGH Genomic Labeling kit (p/n 18095-012), Cy3/Cy5 paired labeling reactions were combined and the labeled targets were purified using the Microcon YM-30 filter units (p/n 42410).

To each labeled target the following blocking reagents were added: 50 ug Invitrogen CotI DNA (p/n 15279-011), 100 µg Invitrogen yeast tRNA (p/n 15401011), and 50 µl of Agilent's 10X Control Targets (p/n 5185-5976). The targets were concentrated using the Millipore Microcon YM-30 filter units until the total volume of each sample was <37.5 µl.

Example 2

Low Volume Hybridization with Immiscible Liquid Formulation Fluorinert FC-40 or FC-77

After elution from the Microcon filter unit, the volume was brought to 37.5 µl with dH$_2$O and 37.5 µl Agilent 2X Hybridization Buffer, (p/n 5188-5220) was added. The samples were heat denatured for 3 minutes at 95° C. and immediately placed at 37° C. for 30 minutes for a pre-annealing step. 425 µl of Fluorinert FC-77 or FC-40, the immiscible liquid formulations, were added to the samples. The samples were mixed by pipetting up and down but upon completion of the mixing two phases quickly formed for each of the samples. The hybridizations were assembled, using the Agilent hybridization chambers (p/n G2534A), gasket slides (p/n G2534-60003) and arrays (p/n G4410B) as outlined in the 'Oligonucleotide Array-Based CGH for Genomic DNA Analysis' Protocol Version 2.0 (August 2005). The hybridization was performed at ~15 RPMs at 65° C. for 17 hours.

Following hybridization the arrays were disassembled and washed as outlined in the above protocol. In short: The gasket/array sandwich was disassembled under wash solution #1 (0.5× SSPE, 0.005% N-Lauryl Sarcosine), the array was placed in a slide rack submerged in wash solution #1 and washed at room temperature with moderate stir bar mixing for 5 minutes, the slide rack was transferred to a bath containing wash solution #2 (0.1× SSPE, 0.005% N-Lauryl Sarcosine) at 37° C. and the washed for 3 minutes with moderate stir bar mixing. The arrays were then slow pulled from the wash bath and scanned in an Agilent microarray scanner (p/n G2565BA). Data was extracted from the scanned images using Agilent's Feature Extraction software 8.1.

Figure 8:
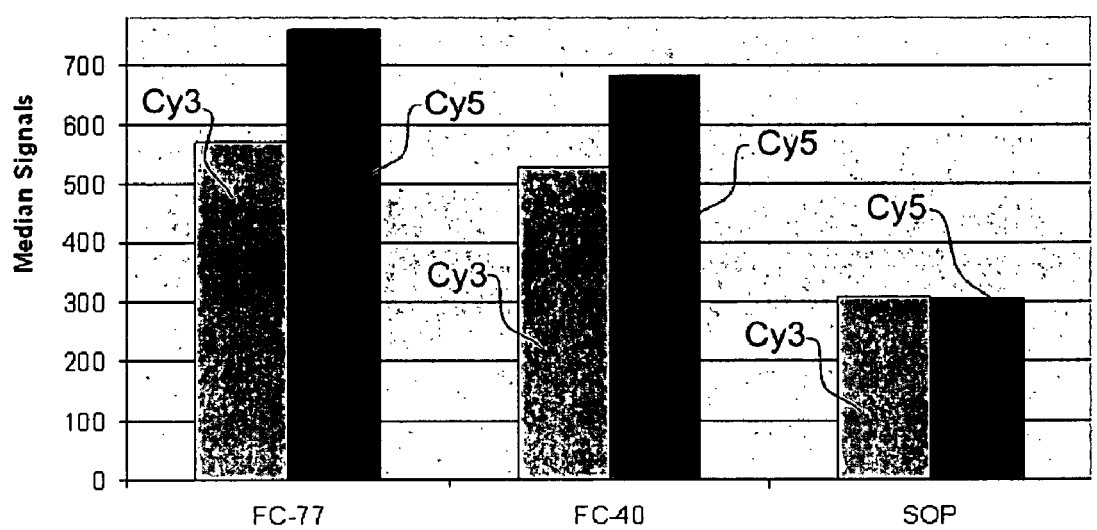
FIG. 8 shows the Cy3 and Cy5 median signals for small volume 17 hr hybridizations done with two different immiscible solutions. As a comparison, also shown are the median signals for a large volume 40 hr hour hybridization without immiscible fluid.

Visually the scanned images looked comparable to our SOP (standard operating procedure) array CGH hybridizations performed without immiscible liquid, using 500 µl of target solution. FIG. 8 shows the Cy3 and Cy5 median signals for the two 0.5 µg, 17 hour hybridizations which were done with the two immiscible solutions, FC-77 & FC-40. As a comparison, the median signals for a 2 ug, 40 hour SOP hybridization are also shown. The 0.5 ug immiscible liquid hybridizations which are hybridized for half the time, give approximately twice the signal of the 2 ug SOP hybridization.

Figure 9:
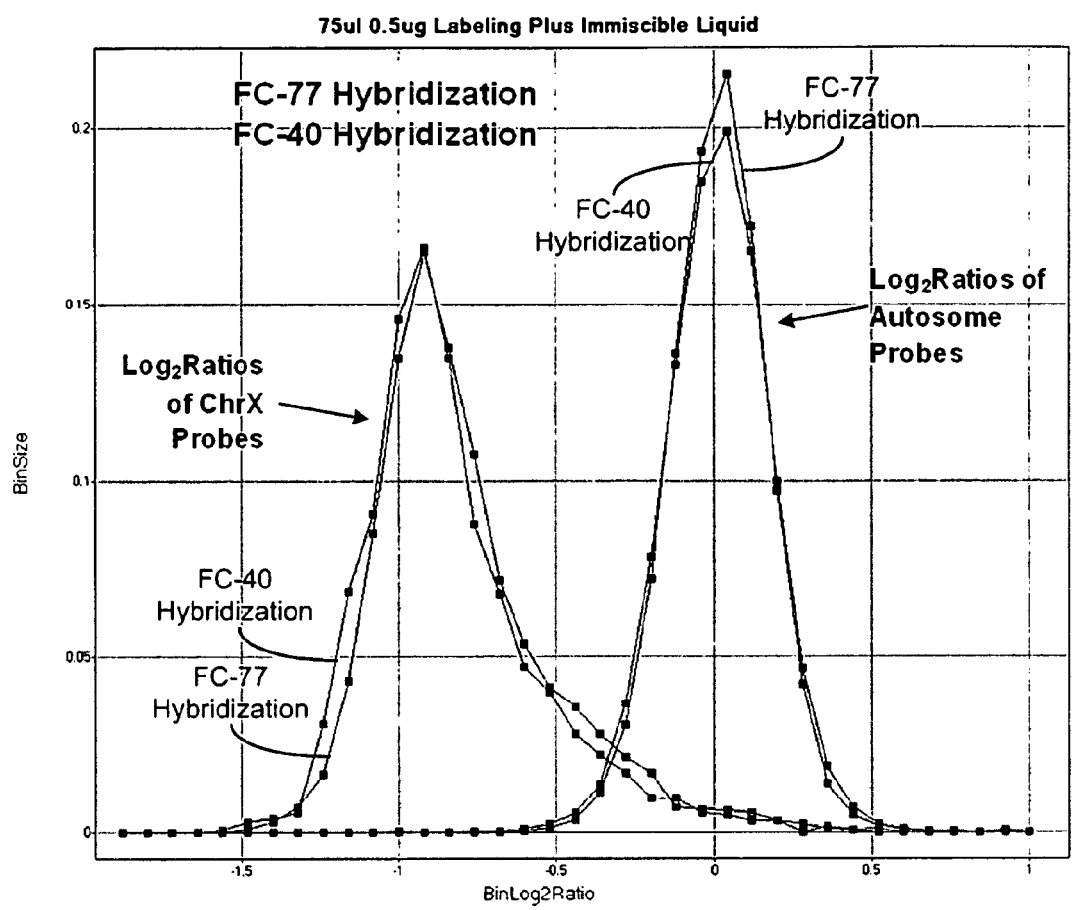
FIG. 9 shows the $\log_2$ratio distributions of the ChrX and Autosome probes for small volume 17 hr hybridizations done with two different immiscible solutions.

FIG. 9 shows the $\log_2$ratio distributions of the ChrX and Autosome probes. Since this is a Male (Cy5)/Female (Cy3) hybridization, one vs. two copies of the X chromosome, the expected median for the ChrX log2ratios is −1.0. The median values observed are −0.85 & −0.89 for the FC-77 & FC-40 hybridizations respectively, which are comparable to the values observed under SOP hybridization conditions. This data shows that the hybridization conditions described in this invention are not introducing hybridization artifacts that adversely affect the results.

Example 3

Low Volume Hybridization with Immiscible Liquid Formulation H-Galden ZT-180

Sample prep was performed as outlined in Example 1, except only 50% of a 0.5 ug labeled target was used for the hybridization. The low volume hybridization was performed as outlined in Example 2, except: 1) The immiscible liquid was ZT-180. 2) The 75 µl aqueous target solution was applied to the gasket slide followed by 425 µl of the immiscible liquid (the two were not combined prior to addition to the gasket slide). 3) Hybridization time was 18 hours.

The median Cy3 and Cy5 signals were 284 and 464 respectively. The values were about half of the median signals of the FC-77 and FC-40 hybridizations described in Example 2, as was expected since half the amount of target was used. The median observed ChrX $\log_2$ratio was −0.89.

Example 4

Low Volume Hybridization with Immiscible Liquid Formulation Asahi CT-180

Sample prep was performed as outlined in Example 1, except only 50% of a 0.5 ug labeled target was used for the hybridization. The low volume hybridization was performed as outlined in Example 2, except: 1) The immiscible liquid was CT-180. 2) The 75 µl aqueous target solution was applied to the gasket slide followed by 425 µl of the immiscible liquid. 3) The RPM setting was 12. 4) Hybridization time was 20 hours.

The median Cy3 and Cy5 signals were 229 and 362 respectively and the median observed ChrX $\log_2$ratio was −0.86.

Example 5

Low Volume Hybridization with Immiscible Liquid Formulation 1:1 H-Galden ZT-180: Asahi CT-180

Sample prep was performed as outlined in Example 1, except only 50% of a 0.5 µg labeled target was used for the hybridization. The low volume hybridization was performed as outlined in Example 2, except: 1) The immiscible liquid was a 1:1 combination of ZT-180 and CT-180. 2) The 75 µl aqueous target solution was applied to the gasket slide followed by 425 µl of the combined immiscible liquids. 3) The RPM setting was 12. 4) Hybridization time was 18 hours.

The median Cy3 and Cy5 signals were 143 and 227 respectively and the median observed ChrX $\log_2$ratio was −0.90.

Example 6

Low Volume Hybridization with Immiscible Liquid Formulation 1:1 H-Galden ZT-180: Novec HFE-7500

Sample prep was performed as outlined in Example 1, except only 50% of a 0.5 µg labeled target was used for the hybridization. The low volume hybridization was performed as outlined in Example 2, except: 1) The immiscible liquid was a 1:1 combination of ZT-180 and HFE-7500. 2) The 75 µl aqueous target solution was applied to the gasket slide followed by 425 µl of the combined immiscible liquids. 3) Hybridization temperature was 67° C. 4) The RPM setting was 12.

The median Cy3 and Cy5 signals were 130 and 203 respectively and the median observed ChrX $\log_2$ratio was −0.89.

Example 7

Low Volume Hybridization with Immiscible Liquid Formulation H-Galden ZT-180 with Varying Aqueous/Immiscible Liquid Ratios Sample prep was performed as outlined in Example 1. The low volume hybridizations were performed as outlined in Example 2, except: 1) The immiscible liquid was ZT-180. 2) Different aqueous target solution volumes were used: 37.5 µl, 75 µl, 100 µl and 150 µl. 3) The aqueous target solutions were applied to the gasket slide followed by the immiscible liquid to bring the final hybridization volume to 500 µl.

The median Cy3/Cy5 signals for the 37.51 µl, 75 µl, 100 µl and 150 µl aqueous hybridizations were 537/801, 550/821, 584/869 and 372/545 respectively and the median observed ChrX $\log_2$ratios were −0.84, −0.89, −0.89, and −0.90, respectively.

Example 8

Low Volume Hybridization with Immiscible Liquid Formulation H-Galden ZT-180 or Galden HT-170; with Varying Hybridization Volumes Sample prep was performed as outlined in Example 1, except only 46% of a 0.5 ug labeled target was used for the hybridizations. The low volume hybridization was performed as outlined in Example 2, except: 1) The immiscible liquids were ZT-180 and HT-170. 2) The final hybridization volumes were 525 µl or 450 µl. 3) The 75 µl aqueous target solution was applied to the gasket slide followed by 450 µl or 375 µl of the immiscible liquid.

The median Cy3/Cy5 signals for the ZT-180 525 µl or 450 µl hybridizations were 151/215 and 212/296, respectively and the median observed ChrX $\log_2$ratios were −0.89 and −0.90, respectively. The median Cy3/Cy5 signals for the HT-170 525 µl or 450 µl hybridizations were 217/311 and 255/361, respectively and the median observed ChrX $\log_2$ratios were −0.87 and −0.86, respectively.

Example 9

Low Volume Hybridization with Immiscible Liquid Formulation H-Galden ZT-180 and Fluorosurfactant FC-4430 (3M Company)

Sample prep was performed as outlined in Example 1, except only 50% of a 0.5 ug labeled target was used for the hybridizations. The low volume hybridization was performed as outlined in Example 2, except: 1) The immiscible liquid was ZT-180. 2) Agilent 2X hybridization buffer (p/n #5185-5973) was used, with the addition of fluorosurfactant FC-4430 at a final concentration of 0.3% in the aqueous phase. 3) The final hybridization volume was 400 µl. 4) The 75 µl aqueous target solution was applied to the gasket slide followed by 325 µl of the immiscible liquid. 5) The RPM setting was 20. 6) Hybridization time was 20 hours.

The median Cy3 and Cy5 signals were 327 and 520, respectively and the median observed ChrX $\log_2$ratio was −0.9.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The claimed invention is:

1. A method of commingling a target solution dissolved in an aqueous phase with an array, the method comprising:
    introducing a quantity of the target solution dissolved in an aqueous phase and a quantity of an immiscible liquid into a cavity having an array on an interior surface, so that the quantities of target solution and immiscible liquid do not fill the volume, and so that a gas is contained within the volume; and
    agitating the cavity to form liquid bubbles of the immiscible liquid in said aqueous phase.

2. The method of claim 1, wherein the aqueous phase and immiscible liquid exhibit substantially different surface tensions.

3. The method of claim 1, wherein the aqueous phase includes a blocking reagent or a hybridization buffer.

4. The method of claim 1, wherein the aqueous phase fills one-fourth of the cavity or less.

5. The method of claim 1, wherein, together, the quantity of immiscible liquid and aqueous phase fill at least one-half of the cavity.

6. The method of claim 1, wherein the gas fills one-half of the cavity or less.

7. The method of claim 1, wherein the immiscible liquid is nonflammable.

8. The method of claim 1, wherein the immiscible liquid comprises a fluorocarbon liquid.

9. The method of claim 1, wherein the immiscible liquid comprises a perfluorocarbon liquid.

10. The method of claim 1, wherein the immiscible liquid comprises a hydrofluoropolyether liquid.

11. The method of claim 1, wherein the immiscible liquid comprises a perfluoropolyether liquid.

12. The method of claim 1, wherein the immiscible liquid comprises a hydrofluoroether liquid.

13. The method of claim 1, wherein the immiscible liquid comprises a perfluoroalkylamine liquid.

14. The method of claim 1, wherein the immiscible liquid comprises a mixture of a hydrofluoropolyether liquid and a perfluoroalkylamine liquid.

15. The method of claim 1, wherein the agitation of the cavity comprises rotating the cavity at a frequency chosen so that the immiscible liquid forms a plurality of liquid bubbles.

16. The method of claim 15, wherein the cavity is rotated at a frequency chosen so that a portion of the plurality of bubbles exhibits free motion about the cavity.

17. The method of claim 15, wherein the cavity is rotated at a frequency chosen so that the immiscible liquid forms between 10 and 1,000 bubbles within the cavity.

18. The method of claim 15, wherein the cavity is approximately 600 microliters.

19. The method of claim 15, wherein the cavity is rotated at a frequency chosen so that a single air bubble is exhibited in the cavity.

20. The method of claim 1, further comprising the act of heating the cavity.

21. The method of claim 1, wherein said agitating moves said liquid bubbles of the immiscible liquid in said aqueous phase.

22. The method of claim 1, wherein said array is a two-dimensional, addressable array.

* * * * *